United States Patent [19]

Sakuma et al.

[11] Patent Number: 5,213,801
[45] Date of Patent: May 25, 1993

[54] CONTACT LENS MATERIAL

[75] Inventors: Shuji Sakuma; Kiminori Atsumi; Akira Inose, all of Tokyo, Japan

[73] Assignee: Kabushiki Kaisha Sangi, Tokyo, Japan

[21] Appl. No.: 732,546

[22] Filed: Jul. 19, 1991

[30] Foreign Application Priority Data

Jul. 19, 1990 [JP] Japan .................................. 2-189404

[51] Int. Cl.$^5$ .......................... G02C 7/04; A61K 47/32
[52] U.S. Cl. ................................ 424/429; 351/160 H; 523/106; 525/937
[58] Field of Search .................... 351/160 H; 424/429; 523/106; 525/937; 501/1

[56] References Cited

U.S. PATENT DOCUMENTS

| | | | |
|---|---|---|---|
| 2,066,271 | 12/1936 | Irwin | 99/220 |
| 4,131,696 | 12/1978 | Covington | 351/160 H |
| 4,273,734 | 6/1981 | Seiderman | 264/1.1 |
| 4,525,410 | 6/1985 | Hagiwara et al. | 428/198 |
| 4,701,038 | 10/1987 | Neefe | 434/429 |

FOREIGN PATENT DOCUMENTS

| | | |
|---|---|---|
| 0251783 | 1/1988 | European Pat. Off. . |
| 0275047 | 7/1988 | European Pat. Off. . |
| 61-027906 | 2/1986 | Japan . |
| 8002840 | 12/1980 | World Int. Prop. O. . |

*Primary Examiner*—Mark L. Bell
*Assistant Examiner*—Deborah Jones
*Attorney, Agent, or Firm*—Finnegan, Henderson, Farabow, Garrett & Dunner

[57] ABSTRACT

An antibacterial contact lens material comprising a hydrogel lens material and an antibacterial ceramic containing at least one metal selected from the group consisting of Ag, Cu and Zn. The lens material contains from 0.001–10.0% by weight of the antibacterial ceramic and the ceramic from 0.0001 to 10.0% by weight of the metal based on the weight of the ceramic.

9 Claims, No Drawings

CONTACT LENS MATERIAL

BACKGROUND OF THE INVENTION

1. Field of the Invention

The present invention relates to a contact lens material having an antibacterial property, in which an antibacterial ceramic containing at least one metal selected from the group consisting of Ag, Cu and Zn is mixed with or coated onto a hydrogel lens material.

2. Description of the Prior Art

It is well known that contact lenses can be used instead of a pair of spectacles. A hard contact lens comprising polymethacrylic acid methyl esters as a main component, a soft contact lens comprising poly 2-hydroxy ethyl methacrylate as a main component, or a contact lens comprising natural polymers such as collagen, glass or ceramics are known.

When a contact lens is fitted to a cornea, a thin film of tear fluid remains between the lens and the cornea. Further, the outer surface of the contact lens is in contact with the atmosphere. The lens once installed on the eye is likely to be attacked by undesired materials such as bacteria and dust in the air and entails breeding of bacteria along the surfaces of the contact lens so that a risk occurs of developing a surface injury to the eye. Also it is necessary that a supply of fresh air be available to the cornea beneath the contact lens to promote metabolism of the cornea tissues. For these reasons, various materials have been examined as suitable contact lens materials. However, materials that allow a supply of fresh air to the cornea to prevent cornea damage and that exclude undesired materials have not heretofore been found.

SUMMARY OF THE INVENTION

The object of the present invention is to provide a contact lens material that prevents breeding of bacteria to protect the cornea tissues.

As the result of various studies, applicants found that contact lens material that prevents the breeding of bacteria to protect the cornea tissues can be obtained when an antibacterial ceramic material containing at least one metal selected from the group consisting of Ag, Cu and Zn is mixed through a kneading process with a hydrogel lens material which can then be made by the usual process into a contact lens. Alternatively, the antibacterial ceramic can be coated on the surfaces of a hydrogel lens material.

DETAILED DESCRIPTION OF THE INVENTION

It is necessary that the ceramics used in this invention be uniformly dispersed in the hydrogel lens material and be harmless to the cornea tissue. Therefore silica based ceramics, such as zeolite and silicates, calcium carbonate based ceramics, and phosphate based ceramics such as calcium phosphate and apatite, can be used in this invention.

In view of the affinity of the antibacterial metal to the living body, the dispersibility of the antibacterial metal in the hydrogel lens materials, and the non-dissolution of the antibacterial metal in the thin film of tear fluid around the contact lens, it is preferred that apatite based ceramics such as hydroxyapatite and fluoroapatite be used as the ceramic material. Moreover, when the transparency required for proper vision is considered, it is preferred that silica based ceramics be used. As a method for retaining the antibacterial metal such as Ag, Cu and Zn in the ceramics to prevent its dissolution into water or a fluid, it is preferred to use the ion exchange method. When the antibacterial metal is adsorbed or fixed to the ceramics by the ion exchange method, the ceramics are not effected by any possible anion influence upon the metal salt used. Thus, when antibacterial ceramics prepared by the ion exchange method are compared to ceramics in which the metal salt is merely absorbed, the amount of dissolution of the metal into water or a fluid from the antibacterial ceramics prepared is extremely small. This is because the metal is not desorbed from the ceramics material prepared by such a method.

Since the ceramics as mentioned above have the property of inorganic ion exchange, the antibacterial ceramics used in this invention can be prepared easily by the ion exchange method. This method for preparing the antibacterial ceramics is explained in more detail below, in which hydroxyapatites are mainly used as the ceramics. The fine powders of hydroxyapatite synthesized by the usual method or of natural hydroxyapatite are packed into a column uniformly and an aqueous solution of the metal salt, such as silver nitrate or copper chloride, is poured into the column, or an aqueous solution of the metal salt is added to a suspension of the fine hydroxyapatite powders and subjected to strong stirring for several hours. Antibacterial hydroxyapatites, in which a part of the $Ca^{++}$ in the crystal lattice is replaced by the metal ion of the metal salt used, are thus produced. The amount of metal ion substituted for $Ca^{++}$ is a factor of the temperature and time, and of the type and amount of the metal salt used. The antibacterial hydroxyapatites obtained in this method are thereafter fully washed with water to remove any non-adsorbed salts or replaced calcium and are then dried and crushed. While a method for adsorbing the metal in the hydroxyapatites by the ion exchange method is discussed above, it may be easily foreseen by one skilled in the art that the antibacterial hydroxyapatites can be produced by precipitating hydroxyapatites in a solution of the water soluble metal salt.

The metal in the ceramics according to the present invention is virtually nondissolvable in water or tear fluid. The antibacterial ceramics are heat resistant and the antibacterial property is not lost by any heat firing process. Actually, when the antibacterial ceramics are heat fired, the bonding strength of the metal in the ceramics is increased. Accordingly, the antibacterial ceramics can be used after heat firing and crushing. Also, silica based antibacterial agents containing the metal can be obtained in a similar method by using silica based ceramics in place of hydroxyapatites.

The substituted amounts of metal such as Ag, Cu and Zn in the antibacterial ceramics obtained in this method can be easily measured by the usual analytical method.

It is preferred that fine ceramic powders, preferably 5 $\mu$m or less, be used and sufficient antibacterial property is obtained when the amounts of metal contained in the ceramics are 0.0001% or more, by weight.

Conversely, overly large amounts of metal in the ceramics is not preferred, because the crystalline structure of the ceramics may be affected and the physical property of the ceramics may change. Generally, the amounts of metal substituted are 10% or less, preferably 0.0001%–5% by weight.

The antibacterial ceramics produced in this method are uniformly mixed by a kneading process with a hydrogel lens material usually used to make a contact lens such as polysiloxanyl methacrylate, poly 2-hydroxyethyl methacrylate and the like, and the contact lens is finished by cutting and polishing. The metal salts in the antibacterial ceramics are exposed on the surfaces of the contact lens. It is not preferable to add too large amount of the antibacterial ceramics to the hydrogel lens material, because the physical properties of the contact lens such as the light transparency and elasticity to meet the eyes will be adversely affected. Generally, for the purpose of achieving an antibacterial property from 0.001-10% of the antibacterial ceramics should be added to the hydrogel lens material.

When a contact lens containing the antibacterial ceramics produced by the above method is fitted to the cornea, the light transparency and wear feeling is not effected, and a strong antibacterial property is provided. That is, the antibacterial ceramics mixed with the contact lens material generate exocyclic oxygen atoms or superoxide radicals or respiratory malfunctioning enzymes which cause the bacteria and fungi to die, ["The Molecular Mechanisms of Copper and Silver ion disinfection of Bacteria and Viruses" CRC Critical Reviews in Environmental Control 18, 295 (1989)] Bacteria and fungi are always present in the air and therefore always in contact with the eyes. However, when the contact lens of this invention is installed in the eye, the antibacterial property is continuously available.

Adding an antibacterial ceramic to the hydrogel lens material by a kneading process is explained above. However, the purpose of this invention may also be achieved by coating the material's surfaces with a bonding agent containing an acrylic based emulsion and the antibacterial ceramics, or by coating the surfaces by a sputtering method with the antibacterial ceramics.

The contact lens of this invention is easily obtained by adding the antibacterial ceramics to the hydrogel lens material. The amounts of the metal contained in the antibacterial ceramics can be optionally changed so as to serve the purpose of the present invention, while the metal carried by it is not dissolved into water or fluid from the ceramics. Accordingly, contact lens having an antibacterial property, which is desired in a contact lens, can be produced, and in addition the living body is not effected due to the non-dissolution of the metal contained in the ceramics with tear fluid.

EXAMPLE 1

Antibacterial hydroxyapatite containing Ag 2% and Zn 2%, each by weight, was heat fired at 1200° C. and powdered to provide a fine ceramic material. The fine powders were added to three mixtures of 2-hydroxyethyl methacrylate and ethyleneglycoldimethacrylate at the rates of 0.01%, 0.3% and 1.5% by weight, respectively. Polymerization was performed in a constant temperature water bath and hydrogel lens material having an antibacterial property was obtained. The hydrogel lens material obtained was then formed in button shape configurations and contact lenses having an antibacterial property were obtained by cutting and polishing the button shaped configurations. The results which were obtained by examining the dissolution rate of the antibacterial metal into water, the light transparency, the oxygen permeability and the antibacterial and stimulative properties of the contact lenses according to the present invention are shown in the Table below.

EXAMPLE 2

Antibacterial hydroxyapatites containing Ag 2% and Cu 2% each by weight were powdered into a fine ceramic material. Fine powders of 0.01% by weight, 0.1% by weight and 1.0% by weight were added to mixed monomers of siloxanyl methacryate, methyl methacrylate and ethyleneglycoldimethacrylate. Polymerization was performed in a constant temperature water bath and hydrogel lens material having an antibacterial property was obtained. The hydrogel lens material obtained was formed into button shape configurations and three contact lenses having an antibacterial property and an oxygen permeability were obtained by cutting and polishing the button shaped configurations. The metal dissolution rate, the light transparency, the oxygen permeability and the antibacterial and stimulative properties of the contact lenses obtained are shown in the Table given below.

EXAMPLE 3

Antibacterial silicas containing Ag 2% and Zn 1% by weight were powdered to form fine powders. Fine powders of 0.01% by weight, 0.1% by weight and 1.0% by weight were added by a kneading process to mixed monomers of 2-hydroxyethylmethacrylate, N-vinylpyrolidene methyl methacrylate and ethyleneglycoldimethacrylate. Polymerization was performed in a constant temperature water bath and hydrogel lens materials having an antibacterial property was obtained. The material was formed in button shapes and three contact lenses having an antibacterial property were obtained by cutting and polishing the button shaped configurations. The dissolution rate of metal into water, the light transparency, the oxygen permeability and the antibacterial and stimulative properties of the contact lenses obtained are shown in the Table given below.

EXAMPLE 4

Antibacterial silicas containing Ag 2% by weight and Cu 1% by weight were powdered to form fine powders. Fine powders of 0.01% by weight, 0.1% by weight and 1.0% by weight were added by a kneading process to the mixed monomers of siloxanylmetharylate, trifluoromethylmethacrylate, methylmethacrylate and ethyleneglycoldimethacrylate. Polymerization was performed in a constant temperature water bath and hydrogel lens material having an antibacterial property was obtained. The hydrogel lens material was formed into button shapes and contact lenses having an antibacterial property and an oxygen permeability were obtained by cutting and polishing the button shaped configurations. The dissolution rate of metal into water, the light transparency, the oxygen permeability and the antibacterial and stimulative properties of the contact lenses obtained are shown in the Table given below.

EXAMPLE 5

In this example, a disc shaped form of an antibacterial hydroxyapatite containing Ag 3% by weight, which had been heat fired at 1000° C. for 5 hours, was used in a RF sputtering apparatus. The RF sputtering apparatus was operated for 30 minutes under the following conditions: Ar gases $4 \times 10^{-3}$ torr; the temperature of the substrate 40° C.; the electric power 200 W. Antibacterial hydroxyapatites from the disc were coated by the sputtering apparatus onto the surfaces of a hydrogel contact lens material comprising polysiloxanylmethacrylate and polymethylmethacrylate as the main components and three lenses were made. The dissolution rate of metal into water, the light transparency, the oxygen permeability, and the antibacterial and stimulative properties of the hydrogel contact lenses are shown in the Table below.

CONTROL TEST 1

Mixed monomers of 2-hydroxyethylmethacrylate and ethyleneglycoldimethacrylate were poured into a test tube and polymerized in a constant temperature water bath. From the polymers obtained, contact lenses were prepared. The light transparency, the oxygen permeability, and the antibacterial and stimulative properties of the contact lenses are shown in the Table below.

CONTROL TEST 2

Mixed monomers of siloxanyl methacrylate, methylmethacrylate and ethyleneglycoldimethacrylate were poured to a test tube and polymerized in a constant temperature water bath. From the polymers obtained, contact lenses were prepared. The light transparency, the oxygen permeability, and the antibacterial and stimulative properties of the contact lenses obtained are shown in the Table below.

0.0001 to 10% by weight of the ceramic of at least one metal selected from the group consisting of silver, copper, and zinc.

2. The contact lens material of claim 1, wherein the ceramic is hydroxyapatite.

3. The contact lens material of claim 1, wherein said metal is present is an amount of from 0.0001 to 5.0% by weigh of the ceramic.

4. The contact lens material of claim 2, wherein said metal is present in an amount of from 0.0001 to 5.0% by weight of the ceramic.

5. The contact lens material of claim 1, wherein the antibacterial ceramic is mixed with the hydrogel lens material by a kneading process.

6. The contact lens material of claim 1, wherein the antibacterial ceramic is coated on a surface of the hydrogel lens material.

7. The contact lens material of claim 1, wherein the ceramic is silica.

8. The contact lens material of claim 1, wherein the hydrogel lens material is selected from the group consisting of polymers of 2-hydroxyethylmethacrylate and ethyleneglycoldimethacrylate; 2-hydroxyethylmethacrylate, N-vinylpyrolidiene, methylmethacrylate and ethyleneglycoldimethacrylate; methylmethacrylate; ethyleneglycoldimethacrylate and siloxyanylmethacrylate; and siloxyanylmethacrylate, trifluoromethylmethacrylate, methylmethacrylate and ethyleneglycoldimethacrylate.

9. The contact lens material of claim 1 in the form of a contact lens.

TABLE

|  | antibacterial ceramics added (%) | metal dissolution rate | | light transparency | oxygen permeability | antibacterial property | irritative property |
|---|---|---|---|---|---|---|---|
| Example (1) | 0.01 | Ag | — | 98% | $10 \times 10^{-11}$ | good | none |
|  |  | Zn | — |  |  |  |  |
|  | 0.3 | Ag | — | 98% | $12 \times 10^{-11}$ | good | none |
|  |  | Zn | — |  |  |  |  |
|  | 1.5 | Ag | — | 97% | $15 \times 10^{-11}$ | good | none |
|  |  | Zn | — |  |  |  |  |
| Example (2) | 0.01 | Ag | — | 98% | $27 \times 10^{-11}$ | good | none |
|  |  | Cu | — |  |  |  |  |
|  | 0.1 | Ag | — | 98% | $30 \times 10^{-11}$ | good | none |
|  |  | Cu | — |  |  |  |  |
|  | 1.0 | Ag | — | 97% | $38 \times 10^{-11}$ | good | none |
|  |  | Cu | — |  |  |  |  |
| Example (3) | 0.01 | Ag | — | 99% | $10 \times 10^{-11}$ | good | none |
|  |  | Zn | — |  |  |  |  |
|  | 0.1 | Ag | — | 99% | $13 \times 10^{-11}$ | good | none |
|  |  | Zn | — |  |  |  |  |
|  | 1.0 | Ag | — | 98% | $17 \times 10^{-11}$ | good | none |
|  |  | Zn | — |  |  |  |  |
| Example (4) | 0.01 | Ag | — | 99% | $35 \times 10^{-11}$ | good | none |
|  |  | Cu | — |  |  |  |  |
|  | 0.1 | Ag | — | 99% | $40 \times 10^{-11}$ | good | none |
|  |  | Cu | — |  |  |  |  |
|  | 1.0 | Ag | — | 99% | $45 \times 10^{-11}$ | good | none |
|  |  | Cu | — |  |  |  |  |
| Example (5) |  | Ag | — | 99% | $32 \times 10^{-11}$ | good | none |
| Control test (1) |  |  |  | 98% | $8 \times 10^{-11}$ | none | none |
| Control test (2) |  |  |  | 98% | $25 \times 10^{-11}$ | none | none |

—: Below detection limit
detection limit:
Ag: 0.01 ppm
Zn: 0.2 ppm
Cu: 0.1 ppm

What is claimed is:

1. A contact lens material comprising a hydrogel lens material and from 0.001 to 10% by weight of an antibacterial ceramic, said antibacterial ceramic comprising a ceramic selected from the group consisting of silica, calcium carbonate, calcium phosphate, hydroxyapatite and fluoroapatite or mixtures thereof that contains from

* * * * *